(12) United States Patent
Treuheit et al.

(10) Patent No.: US 7,723,490 B2
(45) Date of Patent: *May 25, 2010

(54) PROCESS FOR CORRECTION OF A DISULFIDE MISFOLD IN FC MOLECULES

(75) Inventors: Michael J. Treuheit, Newbury Park, CA (US); Sheila R. O'Conner, Moorpark, CA (US); Andrew A. Kosky, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 10/925,183

(22) Filed: Aug. 24, 2004

(65) Prior Publication Data

US 2005/0019334 A1 Jan. 27, 2005

Related U.S. Application Data

(62) Division of application No. 09/709,704, filed on Nov. 9, 2000, now Pat. No. 6,808,902.

(60) Provisional application No. 60/165,188, filed on Nov. 12, 1999.

(51) Int. Cl.
C07K 1/00 (2006.01)
C07K 14/00 (2006.01)
C12N 15/00 (2006.01)
C12P 21/00 (2006.01)

(52) U.S. Cl. ............ 530/412; 435/69.1; 435/69.7; 435/70.1; 530/350; 530/408

(58) Field of Classification Search ............ None
See application file for complete search history.

(56) References Cited

U.S. PATENT DOCUMENTS

| | | | |
|---|---|---|---|
| 4,572,798 A * | 2/1986 | Koths et al. | 530/351 |
| 5,075,222 A | 12/1991 | Hannum et al. | |
| 5,077,392 A | 12/1991 | Rudolph et al. | |
| 5,480,981 A | 1/1996 | Goodwin et al. | |
| 5,654,403 A | 8/1997 | Smith et al. | |
| 5,808,029 A | 9/1998 | Brockhaus et al. | |
| 6,369,027 B1 * | 4/2002 | Boyle et al. | 514/2 |
| 6,627,199 B1 * | 9/2003 | Saris | 424/192.1 |
| 6,660,843 B1 * | 12/2003 | Feige et al. | 530/391.7 |
| 6,808,902 B1 * | 10/2004 | Treuheit et al. | 435/69.7 |
| 2003/0144187 A1 * | 7/2003 | Dunstan et al. | 514/12 |

FOREIGN PATENT DOCUMENTS

| | | |
|---|---|---|
| EP | 0 784 093 A | 7/1997 |
| GB | 1 549 069 A | 8/1979 |
| WO | WO 88/08003 | 10/1988 |
| WO | WO 97/23614 | 7/1997 |
| WO | WO 97/28828 | 8/1997 |
| WO | WO 98/24477 | 8/1998 |
| WO | WO 98/48024 | 10/1998 |
| WO | WO 00/24782 A | 5/2000 |

OTHER PUBLICATIONS

Bass et al., J. Biol. Chem., Sep. 1998, 273(39):25006-25014.*
Arend et al. (1985), J. Immunol. 134(6):3868-3875.
Balavoine et al. (1985), Kluger M.J. Oppenheim JJ, Powanda MC, 'eds'. The Physiological, Metabolic, and Immunologic Actions of Interleukin-1, New York:Alan R. Liss, Inc., pp. 429-436.
Capon et al. (1989), Nature 337:525-531.
Deleuran et al. (1992), Br. J. Rheumatol. 31 :801-809.
Eisenberg et al. (1990), Nature 343 :341-346.
Firestein et al. (1992), J. Immunol. 149(3) :1054-1062.
Fisher et al. (1996), N. Engl. J. Med. 334 :1697-1702.
Hannum et al. (1990) Nature 343(6256) :336-340.
Harvill et al. (1995), Immunotech. 1 :95-105.
Lebsack et al. (1991), Arthritis Reum. 34(suppl) :S67.
Linsley (1991), J. Exp. Med. 174 :561-569.
Mazzei et al. (1990), Eur. J. Immunol. 20 :683-689.
Merewether et al. (2000), Archives of Biochemistry and Biophysics 375(1) :101-110.
Prieru et al. (1987), The Lancet 2 :1240-1242.
Protein Function, a practical approach (1997), p. 77, protocol 6. Ed. T.E. Creighton, Oxford University Press, Oxford.
Schwab et al. (1991), Infect. Immun. 59(12):4436-4442.
Seckinger et al. (1987), J. Immunol. 139(5):1546-1549.
Seckinger et al. (1990), J. Immunol. 145(12):4181-4184.
Van Zee et al. (1996), J. Immunol. 156:2221-2230.
Zheng et al. (1995), J. Immunol. 154:5590-5600.
Rudolph R. et al., "Folding Proteins" in Protein Function. A Practical Approach, Oxford University Press, (Jan. 1, 1997), pp. 57-99, XP001106186.

* cited by examiner

*Primary Examiner*—Gary B Nickol
*Assistant Examiner*—Xiaozhen Xie
(74) *Attorney, Agent, or Firm*—Timothy J. Gaul; Raz Reinecke; Kathleen Fowler

(57) ABSTRACT

The present invention concerns a process by which a misfold in an Fc fusion molecule can be prevented or corrected. In one embodiment, the process comprises (a) preparing a pharmacologically active compound comprising an Fc domain; (b) treating the fusion molecule with a copper (II) halide; and (c) isolating the treated fusion molecule. The pharmacologically active compound can be an antibody or a fusion molecule comprising a pharmacologically active domain and an Fc domain. The preferred copper (II) halide is $CuCl_2$. The preferred concentration thereof is at least about 10 mM for fusion molecules prepared in *E. coli*; at least about 30 mM for fusion molecules prepared in CHO cells. The process can be employed with any number of pharmacologically active domains. Preferred pharmacologically active domains include OPG proteins, leptin proteins, soluble portions of TNF receptors (e.g., wherein the fusion molecule is etanercept), IL-1ra proteins, and TPO-mimetic peptides. The Fc domain preferably has a human sequence, with an Fc sequence derived from IgG1 most preferred. An exemplary Fc sequence is shown in FIG. 5 hereinafter.

12 Claims, 12 Drawing Sheets

Standard Ecoli FcOPG Vs Ecoli FcOPG+10mM Cu

— DAD1 A, Sig=215,4 Ref=550,40 of SO031998\000-1301.D
---- DAD1 A, Sig=215,4 Ref=550,40 of SO031998\002-0301.D

FcOPG after Labeling with CDAP

CHO-OPG-Fc Vs CHO-OPG-Fc + 30mM $CuCl_2$

— DAD1 A, sig=215,4 Ref=550,40 of CHOOPCU3\002-0401.D
------ DAD1 A, sig=215,4 Ref=550,40 of CHOOPCU3\000-0201.D

FIG. 5A

```
    ATGGACAAAACTCACACATGTCCACCTTGTCCAGCTCCGGAACTCCTGGGGGGACCGTCA
  1 ----------+----------+----------+----------+----------+----------+ 60
    TACCTGTTTTGAGTGTGTACAGGTGGAACAGGTCGAGGCCTTGAGGACCCCCCTGGCAGT
``` a   M D K T H T C P P C P A P E L L G G P S -

```
    GTCTTCCTCTTCCCCCCAAAACCCAAGGACACCCTCATGATCTCCCGGACCCCTGAGGTC
 61 ----------+----------+----------+----------+----------+----------+ 120
    CAGAAGGAGAAGGGGGGTTTTGGGTTCCTGTGGGAGTACTAGAGGGCCTGGGGACTCCAG
``` a   V F L F P P K P K D T L M I S R T P E V -

```
    ACATGCGTGGTGGTGGACGTGAGCCACGAAGACCCTGAGGTCAAGTTCAACTGGTACGTG
121 ----------+----------+----------+----------+----------+----------+ 180
    TGTACGCACCACCACCTGCACTCGGTGCTTCTGGGACTCCAGTTCAAGTTGACCATGCAC
``` a   T C V V V D V S H E D P E V K F N W Y V -

```
    GACGGCGTGGAGGTGCATAATGCCAAGACAAAGCCGCGGGAGGAGCAGTACAACAGCACG
181 ----------+----------+----------+----------+----------+----------+ 240
    CTGCCGCACCTCCACGTATTACGGTTCTGTTTCGGCGCCCTCCTCGTCATGTTGTCGTGC
``` a   D G V E V H N A K T K P R E E Q Y N S T -

```
    TACCGTGTGGTCAGCGTCCTCACCGTCCTGCACCAGGACTGGCTGAATGGCAAGGAGTAC
241 ----------+----------+----------+----------+----------+----------+ 300
    ATGGCACACCAGTCGCAGGAGTGGCAGGACGTGGTCCTGACCGACTTACCGTTCCTCATG
``` a   Y R V V S V L T V L H Q D W L N G K E Y -

```
    AAGTGCAAGGTCTCCAACAAAGCCCTCCCAGCCCCCATCGAGAAAACCATCTCCAAAGCC
301 ----------+----------+----------+----------+----------+----------+ 360
    TTCACGTTCCAGAGGTTGTTTCGGGAGGGTCGGGGGTAGCTCTTTTGGTAGAGGTTTCGG
``` a   K C K V S N K A L P A P I E K T I S K A -

```
    AAAGGGCAGCCCCGAGAACCACAGGTGTACACCCTGCCCCCATCCCGGGATGAGCTGACC
361 ----------+----------+----------+----------+----------+----------+ 420
    TTTCCCGTCGGGGCTCTTGGTGTCCACATGTGGGACGGGGGTAGGGCCCTACTCGACTGG
``` a   K G Q P R E P Q V Y T L P P S R D E L T -

```
    AAGAACCAGGTCAGCCTGACCTGCCTGGTCAAAGGCTTCTATCCCAGCGACATCGCCGTG
421 ----------+----------+----------+----------+----------+----------+ 480
    TTCTTGGTCCAGTCGGACTGGACGGACCAGTTTCCGAAGATAGGGTCGCTGTAGCGGCAC
``` a   K N Q V S L T C L V K G F Y P S D I A V -

```
    GAGTGGGAGAGCAATGGGCAGCCGGAGAACAACTACAAGACCACGCCTCCCGTGCTGGAC
481 ----------+----------+----------+----------+----------+----------+ 540
    CTCACCCTCTCGTTACCCGTCGGCCTCTTGTTGATGTTCTGGTGCGGAGGGCACGACCTG
``` a   E W E S N G Q P E N N Y K T T P P V L D -

```
    TCCGACGGCTCCTTCTTCCTCTACAGCAAGCTCACCGTGGACAAGAGCAGGTGGCAGCAG
541 ----------+----------+----------+----------+----------+----------+ 600
    AGGCTGCCGAGGAAGAAGGAGATGTCGTTCGAGTGGCACCTGTTCTCGTCCACCGTCGTC
```

FIG. 5B a    S D G S F F L Y S K L T V D K S R W Q Q -

```
    GGGAACGTCTTCTCATGCTCCGTGATGCATGAGGCTCTGCACAACCACTACACGCAGAAG
601 ---------+---------+---------+---------+---------+---------+ 660
    CCCTTGCAGAAGAGTACGAGGCACTACGTACTCCGAGACGTGTTGGTGATGTGCGTCTTC
``` a    G N V F S C S V M H E A L H N H Y T Q K -

```
    AGCCTCTCCCTGTCTCCGGGTAAA
661 ---------+---------+---- 684
    TCGGAGAGGGACAGAGGCCCATTT
``` a    S L S L S P G K

Reversed-phase isoform

Reversed-phase main peak

Reversed-phase HPLC of untreated (upper trace) and copper treated (lower trace) FcOPG.

—— DAD1 A, Sig=215,4 Ref=550,40 (CX101998\003-0401.D)
---- DAD1 A, Sig=215,4 Ref=550,40 (CX101998\002-0301.D)

Size-exclusion HPLC of FcOPG after 2 years incubation at 29°C; copper treated FcOPG (lower trace) and untreated FcOPG (upper trace).

SEQUENCE LISTING

```
<160> NUMBER OF SEQ ID NOS: 6

<210> SEQ ID NO 1
<211> LENGTH: 684
<212> TYPE: DNA
<213> ORGANISM: Homo sapiens
<220> FEATURE:
```

<221> NAME/KEY: CDS
<222> LOCATION: (1)..(684)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | gac | aaa | act | cac | aca | tgt | cca | cct | tgt | cca | gct | ccg | gaa | ctc | ctg | 48 |
| Met | Asp | Lys | Thr | His | Thr | Cys | Pro | Pro | Cys | Pro | Ala | Pro | Glu | Leu | Leu | |
| 1 | | | | 5 | | | | | 10 | | | | | 15 | | |
| ggg | gga | ccg | tca | gtc | ttc | ctc | ttc | ccc | cca | aaa | ccc | aag | gac | acc | ctc | 96 |
| Gly | Gly | Pro | Ser | Val | Phe | Leu | Phe | Pro | Pro | Lys | Pro | Lys | Asp | Thr | Leu | |
| | | | 20 | | | | | 25 | | | | | 30 | | | |
| atg | atc | tcc | cgg | acc | cct | gag | gtc | aca | tgc | gtg | gtg | gtg | gac | gtg | agc | 144 |
| Met | Ile | Ser | Arg | Thr | Pro | Glu | Val | Thr | Cys | Val | Val | Val | Asp | Val | Ser | |
| | | 35 | | | | | 40 | | | | | 45 | | | | |
| cac | gaa | gac | cct | gag | gtc | aag | ttc | aac | tgg | tac | gtg | gac | ggc | gtg | gag | 192 |
| His | Glu | Asp | Pro | Glu | Val | Lys | Phe | Asn | Trp | Tyr | Val | Asp | Gly | Val | Glu | |
| 50 | | | | | 55 | | | | | 60 | | | | | | |
| gtg | cat | aat | gcc | aag | aca | aag | ccg | cgg | gag | gag | cag | tac | aac | agc | acg | 240 |
| Val | His | Asn | Ala | Lys | Thr | Lys | Pro | Arg | Glu | Glu | Gln | Tyr | Asn | Ser | Thr | |
| 65 | | | | 70 | | | | | 75 | | | | | 80 | | |
| tac | cgt | gtg | gtc | agc | gtc | ctc | acc | gtc | ctg | cac | cag | gac | tgg | ctg | aat | 288 |
| Tyr | Arg | Val | Val | Ser | Val | Leu | Thr | Val | Leu | His | Gln | Asp | Trp | Leu | Asn | |
| | | | | 85 | | | | | 90 | | | | | 95 | | |
| ggc | aag | gag | tac | aag | tgc | aag | gtc | tcc | aac | aaa | gcc | ctc | cca | gcc | ccc | 336 |
| Gly | Lys | Glu | Tyr | Lys | Cys | Lys | Val | Ser | Asn | Lys | Ala | Leu | Pro | Ala | Pro | |
| | | | 100 | | | | | 105 | | | | | 110 | | | |
| atc | gag | aaa | acc | atc | tcc | aaa | gcc | aaa | ggg | cag | ccc | cga | gaa | cca | cag | 384 |
| Ile | Glu | Lys | Thr | Ile | Ser | Lys | Ala | Lys | Gly | Gln | Pro | Arg | Glu | Pro | Gln | |
| | | | 115 | | | | | 120 | | | | | 125 | | | |
| gtg | tac | acc | ctg | ccc | cca | tcc | cgg | gat | gag | ctg | acc | aag | aac | cag | gtc | 432 |
| Val | Tyr | Thr | Leu | Pro | Pro | Ser | Arg | Asp | Glu | Leu | Thr | Lys | Asn | Gln | Val | |
| | | 130 | | | | | 135 | | | | | 140 | | | | |
| agc | ctg | acc | tgc | ctg | gtc | aaa | ggc | ttc | tat | ccc | agc | gac | atc | gcc | gtg | 480 |
| Ser | Leu | Thr | Cys | Leu | Val | Lys | Gly | Phe | Tyr | Pro | Ser | Asp | Ile | Ala | Val | |
| 145 | | | | | 150 | | | | | 155 | | | | | 160 | |
| gag | tgg | gag | agc | aat | ggg | cag | ccg | gag | aac | aac | tac | aag | acc | acg | cct | 528 |
| Glu | Trp | Glu | Ser | Asn | Gly | Gln | Pro | Glu | Asn | Asn | Tyr | Lys | Thr | Thr | Pro | |
| | | | | 165 | | | | | 170 | | | | | 175 | | |
| ccc | gtg | ctg | gac | tcc | gac | ggc | tcc | ttc | ttc | ctc | tac | agc | aag | ctc | acc | 576 |
| Pro | Val | Leu | Asp | Ser | Asp | Gly | Ser | Phe | Phe | Leu | Tyr | Ser | Lys | Leu | Thr | |
| | | | 180 | | | | | 185 | | | | | 190 | | | |
| gtg | gac | aag | agc | agg | tgg | cag | cag | ggg | aac | gtc | ttc | tca | tgc | tcc | gtg | 624 |
| Val | Asp | Lys | Ser | Arg | Trp | Gln | Gln | Gly | Asn | Val | Phe | Ser | Cys | Ser | Val | |
| | | | 195 | | | | | 200 | | | | | 205 | | | |
| atg | cat | gag | gct | ctg | cac | aac | cac | tac | acg | cag | aag | agc | ctc | tcc | ctg | 672 |
| Met | His | Glu | Ala | Leu | His | Asn | His | Tyr | Thr | Gln | Lys | Ser | Leu | Ser | Leu | |
| | | 210 | | | | | 215 | | | | | 220 | | | | |
| tct | ccg | ggt | aaa | | | | | | | | | | | | | 684 |
| Ser | Pro | Gly | Lys | | | | | | | | | | | | | |
| 225 | | | | | | | | | | | | | | | | |

<210> SEQ ID NO 2
<211> LENGTH: 228
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
| Met | Asp | Lys | Thr | His | Thr | Cys | Pro | Pro | Cys | Pro | Ala | Pro | Glu | Leu | Leu |
| 1 | | | | 5 | | | | | 10 | | | | | 15 | |
| Gly | Gly | Pro | Ser | Val | Phe | Leu | Phe | Pro | Pro | Lys | Pro | Lys | Asp | Thr | Leu |
| | | | 20 | | | | | 25 | | | | | 30 | | |

```
Met Ile Ser Arg Thr Pro Glu Val Thr Cys Val Val Asp Val Ser
            35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
             100                 105                 110

Ile Glu Lys Thr Ile Ser Lys Ala Lys Gly Gln Pro Arg Glu Pro Gln
         115                 120                 125

Val Tyr Thr Leu Pro Pro Ser Arg Asp Glu Leu Thr Lys Asn Gln Val
     130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 3
<211> LENGTH: 8
<212> TYPE: PRT
<213> ORGANISM: Artificial Sequence
<220> FEATURE:
<223> OTHER INFORMATION: Preferred Linker

<400> SEQUENCE: 3

Gly Gly Gly Lys Gly Gly Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Preferred Linker

<400> SEQUENCE: 4

Gly Gly Gly Asn Gly Ser Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Preferred Linker

<400> SEQUENCE: 5

Gly Gly Gly Cys Gly Gly Gly Gly
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: Preferred Linker

<400> SEQUENCE: 6

Gly Pro Asn Gly Gly
1               5
```

US 7,723,490 B2

PROCESS FOR CORRECTION OF A DISULFIDE MISFOLD IN FC MOLECULES

The present application is a divisional application of U.S. patent application Ser. No. 09/709,704 (now U.S. Pat. No. 6,808,902), which was filed Nov. 9, 2000 and claimed benefit of priority of U.S. Provisional Application No. 60/165,188, filed Nov. 12, 1999

BACKGROUND OF THE INVENTION

Recombinant proteins are an emerging class of therapeutic agents. Such recombinant therapeutics have engendered advances in protein formulation and chemical modification. Such modifications can protect therapeutic proteins, primarily by blocking their exposure to proteolytic enzymes. Protein modifications may also increase the therapeutic protein's stability, circulation time, and biological activity. A review article describing protein modification and fusion proteins is Francis (1992), *Focus on Growth Factors* 3:4-10 (Mediscript, London), which is hereby incorporated by reference.

One useful modification is in combination with the "Fc" domain of an antibody. Antibodies comprise two functionally independent parts, a variable domain known as "Fab", which binds antigen, and another domain known as "Fc", which links to such effector functions as complement activation and attack by phagocytic cells. An Fc has a long serum half-life, whereas an Fab is short-lived. Capon et al. (1989), *Nature* 337:525-31. When constructed together with a therapeutic protein, an Fc domain can provide longer half-life or incorporate such functions as Fc receptor binding, protein A binding, complement fixation and perhaps even placental transfer. Id. Table 1 summarizes use of Fc fusions known in the art.

Despite their advantages, use of Fc fusion molecules may be limited by misfolding upon expression in a desired cell line. Such misfolded Fc fusion molecules may generate an immune response in vivo or may cause aggregation or stability problems in production.

SUMMARY OF THE INVENTION

The present invention concerns a process by which a misfold in an Fc fusion molecule can be prevented or corrected. In one embodiment, the process comprises:
(a) preparing a fusion molecule comprising (i) a pharmacologically active domain and (ii) an Fc domain;
(b) treating the fusion molecule with a copper (II) halide; and
(c) isolating the treated fusion molecule.

The preferred copper (II) halide is $CuCl_2$. The preferred concentration thereof is at least about 10 mM for fusion molecules prepared in *E. coli*; at least about 30 mM for fusion molecules prepared in CHO cells.

An alternative embodiment of the process comprises the following steps:
(a) preparing a fusion molecule comprising (i) a pharmacologically active domain and (ii) an Fc domain;
(b) treating the fusion molecule with guanidine HCl at a concentration of at least about 4M;
(c) increasing the pH to about 8.5; and
(d) isolating the treated fusion molecule.

Each of these processes can be employed with any number of pharmacologically active domains. Preferred pharmacologically active domains include OPG proteins, leptin proteins, TNF-α inhibitors (e.g., wherein the fusion molecule is etanercept), IL-1 inhibitors (e.g., IL-1ra proteins, which are

TABLE 1

Fc fusion with therapeutic proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol. 154: 5590-600 |
| IgG1 | TNF receptor | septic shock | Fisher et al. (1996), N. Engl. J. Med. 334: 1697-1702; Van Zee, K. et al. (1996), J. Immunol. 156: 2221-30 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al.(1989), Nature 337: 525-31 |
| IgG1, IgG3 | N-terminus of IL-2 | anti-cancer, antiviral | Harvill et al. (1995), Immunotech. 1: 95-105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med. 174: 561-9 | preferred), and TPO-mimetic peptides. Also within the claimed process are molecules in which the pharmacologically active compound is an antibody. The Fc domain preferably has a human sequence, with an Fc sequence derived from IgG1 most preferred. An exemplary Fc sequence is shown in FIG. 5 hereinafter.

Although mostly contemplated as therapeutic agents, compounds of this invention may also be useful in screening for such agents. For example, one could use an Fc-peptide (e.g., Fc-SH2 domain peptide) in an assay employing anti-Fc coated plates. The vehicle, especially Fc, may make insoluble peptides soluble and thus useful in a number of assays.

The compounds prepared by the process of this invention may be used for therapeutic or prophylactic purposes by formulating them with appropriate pharmaceutical carrier materials and administering an effective amount to a patient, such as a human (or other mammal) in need thereof.

Numerous additional aspects and advantages of the present invention will become apparent upon consideration of the figures and detailed description of the invention.

BRIEF DESCRIPTION OF THE FIGURES

FIG. 5. Exemplary nucleic acid and amino acid sequences (SEQ ID NOS: 1 and 2, respectively) of a human IgG1 Fc that may be used in this invention.

DETAILED DESCRIPTION OF THE INVENTION

In General

In production of therapeutic proteins by recombinant techniques, the therapeutic protein quite often must be refolded to an active conformation. At present, the refold process includes an oxidation step to form the disulfide structure of the produced recombinant protein. The reagents commonly used to catalyze formation of the disulfide structure are the free amino acids cysteine/cystamine at a pH of 8-9. In addition, copper sulfate at a copper concentration in the micromolar range can also be used. For refolding of Fc fusion molecules, however, copper sulfate cannot be used due to the high levels of arginine (0.5M) which is a chelator of Cu$^{++}$. Remaining misfolds are normally removed during the subsequent purification process. After process purification of Fc-OPG, for example, a post-peak was isolated by reversed-phase (RP) high performance liquid chromatography (HPLC). Data (primarily from peptide maps and Ellmann's reagent) suggested the RP post-peak did not contain free thiols.

Figure 1:
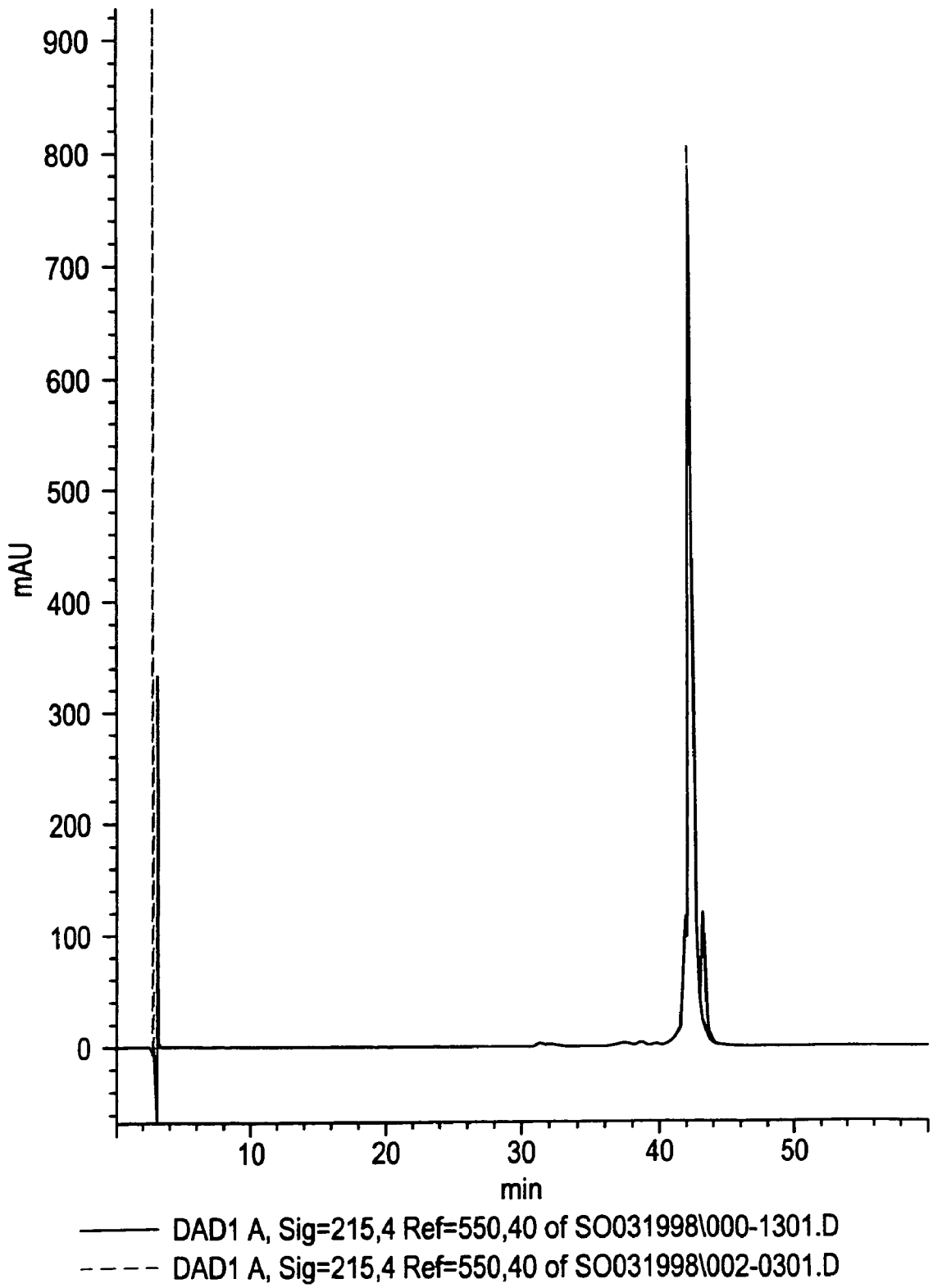
FIG. 1. Reversed-phase high performance liquid chromatography (RP-HPLC) chromatogram showing Fc-OPG prepared in *E. coli* with and without treatment with 10 mM CuCl$_2$. At a concentration of 10 mM, CuCl$_2$ causes complete irreversible elimination of the RP post-peak.
Figure 2:
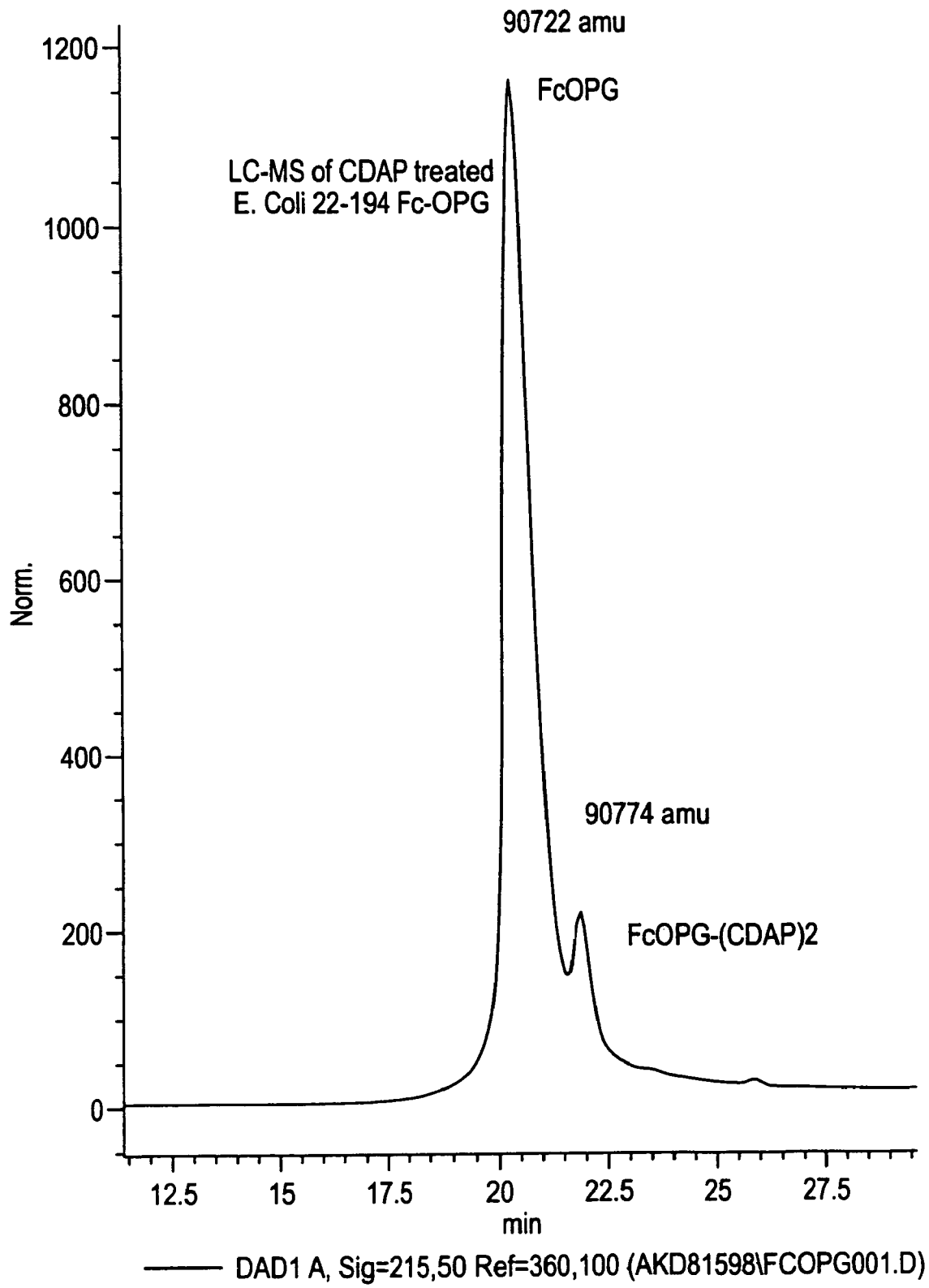
FIG. 2. RP-HPLC chromatogram showing Fc-OPG prepared in *E. coli* treated with CDAP. The RP post-peak molecular weight increased by 52 Da.
Figure 3:
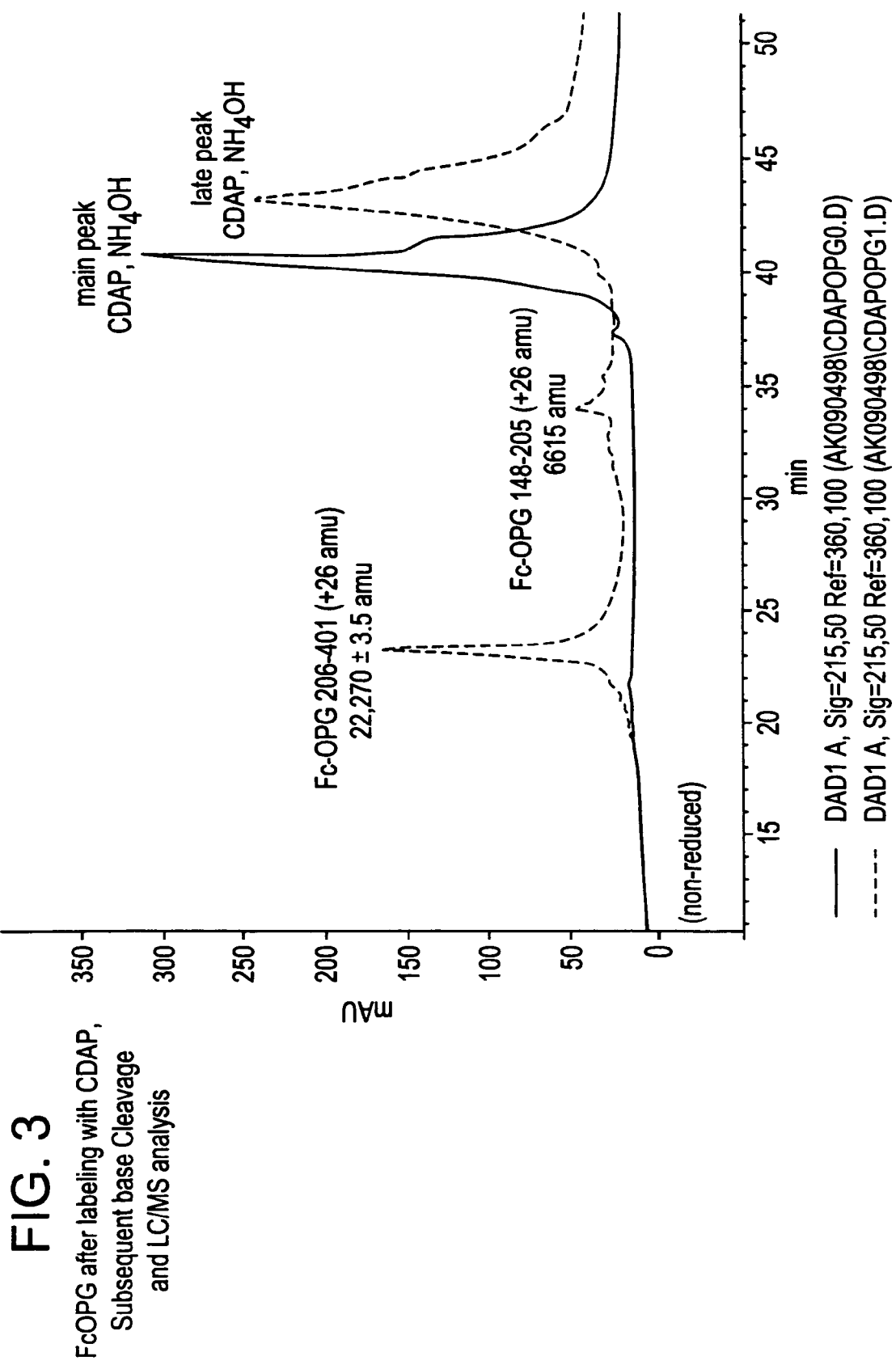
FIG. 3. RP-HPLC chromatogram showing Fc-OPG prepared in *E. coli* treated with CDAP and subsequently subjected to base cleavage. The base cleavage reveals that cysteines 148 and 206 were labeled by CDAP.
Figure 4:
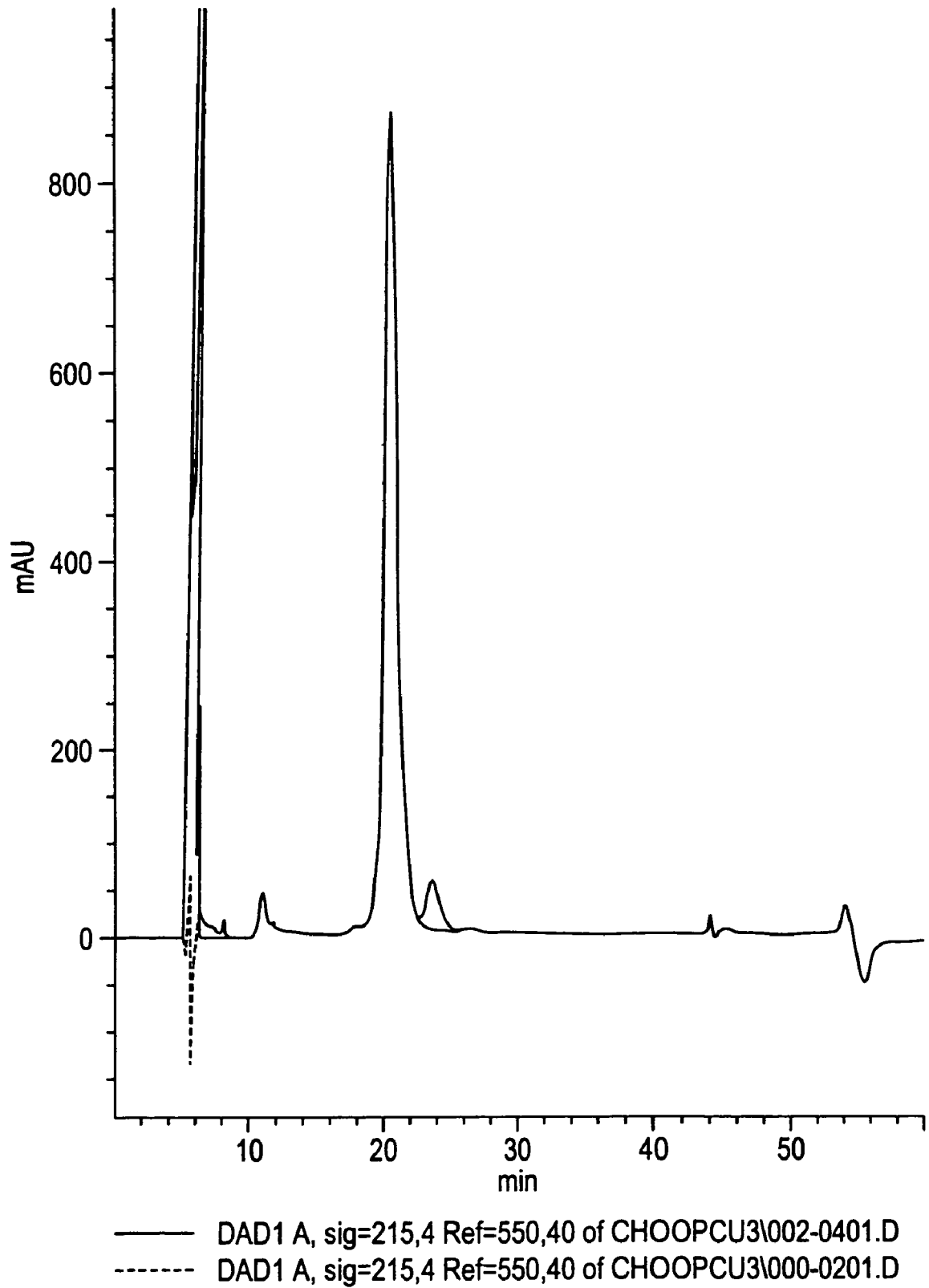
FIG. 4. RP-HPLC chromatogram showing Fc-OPG prepared in CHO cells, with and without treatment with 30 mM CuCl$_2$. At a concentration of 30 mM, CuCl$_2$ causes complete irreversible elimination of the RP post-peak.

In the course of formulation development, the effects of mono- and divalent cations can be related to increases in various chemical degradations. During the screening of Fc-OPG, it was observed that 1 mM CuCl$_2$ had a dramatic effect at reducing the amount of the RP post-peak. Subsequent experiments have shown that 10 mM CuCl$_2$ is required for the complete irreversible elimination of the RP post-peak (see FIG. 1). The RP post-peak was shown to result from an unpaired disulfide through the use of the reagent 1-cyano-4-dimethylamino-pyridinium tetrafluoroborate (CDAP). For each free sulfhydryl, CDAP adds a CN group or increases the molecular weight by 26 Da. Treating Fc-OPG with CDAP and subsequent HPLC/MS analysis indicated that the molecular weight of the Fc-OPG RP post-peak increased by 52 Da or the equivalent of two sulfhydryl groups labeled (see FIG. 2). The molecular weight of the RP main-peak did not change after treating with CDAP. Subsequent base cleavage of the cyanylated RP post-peak indicated that only cysteines 148 and 206 (FIG. 3) are labeled by CDAP. The disulfide, cys148-cys206, which is not formed in the RP post-peak is found in the CH3 region which is the second disulfide loop of Fc and is the same disulfide that was difficult to form in Fc-Leptin. Further, pretreatment with CuCl$_2$ followed by labeling with CDAP produces no detectable change in molecular weight, supporting the conclusion that Cu$^{++}$ fixes the disulfide problem in Fc-OPG. Similar results utilizing CuCl$_2$ have been observed for the CHO—OPG-Fc (FIG. 4) and allows us to conclude that all of our recombinant Fc molecules have the same difficulty in forming the disulfide in the CH3 region of Fc. Surprisingly, CHO cells have the same difficulty in Fc disulfide formation to approximately the same degree.

Alternatively the process could be effected as a post-refold treatment. Several methods can be used to eliminate the RP post-peak. In addition to the CuCl$_2$ treatment, a similar removal of post-peak is observed after denaturing in a minimum of 4 M guanidine HCl and increasing the pH from 5.0 to 8.5. Both treatments strongly support that free thiols are involved which can be converted to a disulfide.

DEFINITION OF TERMS

The terms used throughout this specification are defined as follows, unless otherwise limited in specific instances.

The term "comprising" means that a compound may include additional amino acids on either or both of the N- or C-termini of the given sequence. Of course, these additional amino acids should not significantly interfere with the activity of the compound.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10:4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —$NRR^1$, $NRC(O)R^1$, —$NRC(O)OR^1$, —$NRS(O)_2R^1$, —$NHC(O)NHR$, a succinimide group, or substituted or unsubstituted benzyloxycarbonyl-NH—, wherein R and $R^1$ and the ring substituents are as defined hereinafter; (5) the C-terminus is replaced by —$C(b)R^2$ or —$NR^3R^4$ wherein $R^2$, $R^3$ and $R^4$ are as defined hereinafter; and (6) compounds in which individual amino acid moieties are modified through treatment with agents capable of reacting with selected side chains or terminal residues. Derivatives are further described hereinafter.

The term "peptide" refers to molecules of 3 to 40 amino acids, with molecules of 3 to 20 amino acids preferred and those of 6 to 15 amino acids most preferred. Exemplary peptides may be randomly generated by any of the methods cited above, carried in a phage display library, or derived by digestion of proteins.

The term "native protein" refers to a molecule having an amino acid sequence that may be isolated from an organism without modification by recombinant DNA techniques or other methods.

The term "protein fragment" refers to a molecule or sequence that comprises only a portion of the sequence of a native protein but still retains the pharmacological activity of interest. The term "protein fragment" thus comprises, for example, the soluble domain of a cellular receptor (e.g., a receptor for tumor necrosis factor).

The term "protein variant" refers to a molecule or sequence that is modified from a native protein but still retains the pharmacological activity of interest. Thus, the term "protein variant" comprises a molecule or sequence in which non-native residues substitute for native residues, non-native residues are added, or native residues are deleted. Any native residue may be removed because it provides structural features or biological activity that are not required for the pharmacological activity of interest of the fusion molecules of the present invention. Thus, the term "protein variant" comprises a molecule or sequence that lacks one or more native protein sites or residues that affect or are involved in (1) intracellular signaling, (2) incompatibility with a selected host cell (3) N-terminal heterogeneity upon expression in a selected host cell, (4) glycosylation, (5) interaction with other proteins (e.g., dimerization domains), (6) binding to a receptor or other protein that does not affect the pharmacological activity of interest, or (7) antibody-dependent cellular cytotoxicity (ADCC). Fc variants are described in further detail hereinafter.

The terms "derivatizing" and "derivative" or "derivatized" as used with respect to proteins refers to proteins in which (1) the protein is modified to include a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —$NRR^1$, $NRC(O)R^1$, —$NRC(O)OR^1$, —$NRS(O)_2R^1$, —$NHC(O)NHR$, a succinimide group, or substituted or unsubstituted benzyloxycarbonyl-NH—, wherein R and $R^1$ and the ring substituents are as defined hereinafter; (5) the C-terminus is replaced by —$C(O)R^2$ or —$NR^3R^4$ wherein $R^2$, $R^3$ and $R^4$ are as defined hereinafter; and (6) compounds in which individual amino acid moieties are modified through treatment with agents capable of reacting with selected side chains or terminal residues. Derivatives are further described hereinafter.

The term "polypeptide" refers to native proteins, protein variants, protein derivatives, and protein fragments.

The term "pharmacologically active" means that a substance so described is determined to have activity that affects a medical parameter (e.g., blood pressure, blood cell count, cholesterol level) or disease state (e.g., cancer). Thus, pharmacologically active peptides comprise agonistic or mimetic and antagonistic peptides as defined below.

The term "OPG protein" refers collectively to the novel member of the tumor necrosis factor receptor family described in International patent application WO 97/23614. Exemplary OPG proteins are polypeptides comprising the rat, mouse or human OPG sequences or a consensus of the rat, mouse and human sequences.

The term "TNF-α inhibitor" thus includes solubilized TNF receptors, antibodies to TNF, antibodies to TNF receptor, inhibitors of TNF-α converting enzyme (TACE), and other molecules that affect TNF activity.

TNF-α inhibitors of various kinds are disclosed in the art, including the following references:

European patent applications 308 378; 422 339; 393 438; 398 327; 412 486; 418 014, 417 563, 433 900; 464 533; 512 528; 526 905; 568 928; 663 210; 542 795; 818 439; 664 128; 542 795; 741 707; 874 819; 882 714; 880 970; 648 783; 731 791; 895 988; 550 376; 882 714; 853 083; 550 376; 943 616;

U.S. Pat. Nos. 5,136,021; 5,929,117; 5,948,638; 5,807,862; 5,695,953; 5,834,435; 5,817,822; 5,830,742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435.

International (WO) patent applications 90/13575, 91/03553, 92/01002, 92/13095, 92/16221, 93/07863, 93/21946, 93/19777, 95/34326, 96/28546, 98/27298, 98/30541, 96/38150, 96/38150,97/18207, 97/15561, 97/12902, 96/25861, 96/12735, 96/11209, 98/39326, 98/39316, 98/38859, 98/39315, 98/42659, 98/39329, 98/43959, 98/45268, 98/47863, 96/33172, 96/20926, 97/37974, 97/37973, 96/35711, 98/51665, 98/43946, 95/04045, 98/56377, 97/12244, 99/00364, 99/00363, 98/57936, 99/01449, 99/01139, 98/56788, 98/56756, 98/53842, 98/52948, 98/52937, 99/02510, 97/43250, 99/06410, 99/06042, 99/09022, 99/08688, 99/07679, 99/09965, 99/07704, 99/06041, 99/37818, 99/37625, 97/11668;

Japanese (JP) patent applications 10147531, 10231285, 10259140, and 10130149, 10316570, 11001481, and 127, 800/1991;

German (DE) application 19731521;

British (GB) applications 2 218 101, 2 326 881, 2 246 569.

The disclosures of all of the aforementioned references are hereby incorporated by reference.

The term "interleukin-1 inhibitor" refers to a polypeptide capable of specifically preventing activation of cellular receptors to IL-1, which may result from any number of mechanisms. Such mechanisms include downregulating IL-1 production, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Classes of interleukin-1 inhibitors include:

interleukin-1 receptor antagonists such as IL-1ra, as described below;

CDRs or entire variable regions of anti-IL-1 receptor monoclonal antibodies (e.g., EP 623674), the disclosure of which is hereby incorporated by reference;

IL-1 binding proteins such as soluble IL-1 receptors (e.g., U.S. Pat. No. 5,492,888, U.S. Pat. No. 5,488,032, and U.S. Pat. No. 5,464,937, U.S. Pat. No. 5,319,071, and U.S. Pat. No. 5,180,812, the disclosures of which are hereby incorporated by reference);

CDRs or entire variable regions of anti-IL-1 monoclonal antibodies (e.g., WO 9501997, WO 9402627, WO 9006371, U.S. Pat. No. 4,935,343, EP 364778, EP 267611 and EP 220063, the disclosures of which are hereby incorporated by reference);

IL-1 receptor accessory proteins and antibodies thereto (e.g., WO 96/23067, the disclosure of which is hereby incorporated by reference);

inhibitors of interleukin-1 beta converting enzyme (ICE) or caspase I, which can be used to inhibit IL-1 beta production and secretion;

interleukin-1 beta protease inhibitors;

and other compounds and proteins which block in vivo synthesis or extracellular release of IL-1.

Exemplary IL-1 inhibitors are disclosed in the following references:

U.S. Pat. Nos. 5,747,444; 5,359,032; 5,608,035; 5,843,905; 5,359,032; 5,866,576; 5,869,660; 5,869,315; 5,872,095; 5,955,480

International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, and 99/36415.

European (EP) patent applications 534978 and 894795.

French patent application FR 2762514.

The disclosures of all of the aforementioned references are hereby incorporated by reference.

For purposes of the present invention, IL-1ra and variants and derivatives thereof as discussed hereinafter are collectively termed "IL-1ra protein(s)". The molecules described in the above references and the variants and derivatives thereof discussed hereinafter are collectively termed "IL-1 inhibitors."

The term "TPO-mimetic peptide" comprises peptides that can be identified or derived as described in Cwirla et al. (1997), *Science* 276: 1696-9, U.S. Pat. Nos. 5,869,451 and 5,932,946 and any other reference in Table 2 identified as having TPO-mimetic subject matter, as well as the U.S. patent application, "Thrombopoietic Compounds," filed on Oct. 22, 1999 and hereby incorporated by reference. Those of ordinary skill in the art appreciate that each of these references enables one to select different peptides than actually disclosed therein by following the disclosed procedures with different peptide libraries.

The term "leptin protein" refers to native leptin protein and portions of native leptin protein that retain its anti-diabetes or anti-obesity activity. Exemplary leptin protein sequence is disclosed in PCT/US 97/23183, filed Dec. 11, 1997, which is hereby incorporated by reference.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Structure of Compounds

In General. The process of this invention is useful in preparation of compositions of matter in which an Fc domain may be attached to the pharmacologically active molecule through the molecule's N-terminus or C-terminus. Thus, the Fc fusion molecules of this invention may be described by the following formula I:

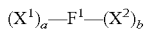   I wherein:

F¹ is an Fc domain;

X¹ and X² are each independently selected from -(L¹)$_c$-P¹ and -(L¹)$_c$-P¹-(L²)$_d$-P²;

P¹ and P² are each independently sequences of pharmacologically active peptides or polypeptides;

L¹ and L² are each independently linkers; and a, b, c, and d are each independently 0 or 1, provided that at least one of a and b is 1.

Thus, compound I comprises preferred compounds of the formulae

   II and multimers thereof wherein F¹ is attached at the C-terminus of X¹;

   III and multimers thereof wherein F¹ is attached at the N-terminus of X²;

   IV and multimers thereof wherein F¹ is attached at the N-terminus of -(L¹)$_c$-P¹;

and

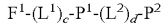   V and multimers thereof wherein F¹ is attached at the N-terminus of -L¹-P¹-L²-P².

Peptides. Any number of peptides may be used in conjunction with the present invention. Of particular interest are peptides that mimic the activity of EPO, TPO, growth hormone, G-CSF, GM-CSF, IL-1ra, leptin, CTLA4, TRAIL, TGF-α, and TGF-β. Peptide antagonists are also of interest, particularly those antagonistic to the activity of TNF, leptin, any of the interleukins (IL-1, 2, 3, . . . ), and proteins involved in complement activation (e.g., C3b). These peptides may be discovered by methods described in the references cited in this specification and other references.

Phage display, in particular, is useful in generating peptides for use in the present invention. It has been stated that affinity selection from libraries of random peptides can be used to identify peptide ligands for any site of any gene product. Dedman et al. (1993), *J. Biol. Chem.* 268:23025-30. Phage display is particularly well suited for identifying peptides that bind to such proteins of interest as cell surface receptors or any proteins having linear epitopes. Wilson et al. (1998), *Can. J. Microbiol.* 44:313-29; Kay et al. (1998), *Drug Disc. Today* 3:370-8. Such proteins are extensively reviewed in Herz et al. (1997), *J. Receptor & Signal Transduction Res.* 17(5):671-776, which is hereby incorporated by reference. Such proteins of interest are preferred for use in this invention.

Numerous peptides of interest are described in the U.S. patent application entitled, "Modified Peptides as Therapeutic Agents," filed Oct. 22, 1999, which is hereby incorporated by reference.

Polypeptides. Numerous polypeptides suitable for use with the subject invention are known in the art. Suitable proteins include hormones (e.g., growth hormone), cytokines (e.g., IL-1ra), and soluble receptors (e.g., tumor necrosis factor receptors I and II). Exemplary polypeptides are those listed in Table 1 (see above).

Fc fusion. An Fc domain may be fused to the N or C termini of the pharmacologically active molecule or at both the N and C termini.

As noted above, Fc variants are suitable vehicles within the scope of this invention. A native Fc may be extensively modified to form an Fc variant in accordance with this invention, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 2 or delete or substitute the cysteine residues at positions 7 and 10 of SEQ ID NO: 2. Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. The Fc domain of SEQ ID NO: 2 (FIG. 5) is one such Fc variant.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the Clq binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, *Molec. Immunol.* 29 (5):633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Linkers. Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines, poly(Gly-Ala), and polyalanines. Other specific examples of linkers are:

```
(Gly)₃Lys(Gly)₄;           (SEQ ID NO: 3)

(Gly)₃AsnGlySer(Gly)₂;     (SEQ ID NO: 4)

(Gly)₃Cys(Gly)₄;           (SEQ ID NO: 5)
and

GlyProAsnGlyGly.           (SEQ ID NO: 6)
```

To explain the above nomenclature, for example, (Gly)₃Lys(Gly)₄ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as —NH—(CH$_2$)$_s$—C(O)—, wherein s=2-20 could be used. These alkyl linkers may further be substituted by any non-sterically hindering group such as lower alkyl (e.g., $C_1$-$C_6$) lower acyl, halogen (e.g., Cl, Br), CN, NH$_2$, phenyl, etc. An exemplary non-peptide linker is a PEG linker,

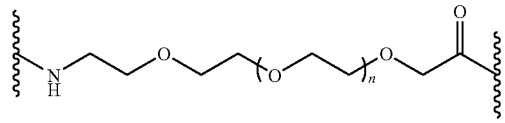

wherein n is such that the linker has a molecular weight of 100 to 5000 kD, preferably 100 to 500 kD. The peptide linkers may be altered to form derivatives in the same manner as described above.

Derivatives. The inventors also contemplate derivatizing the peptide, polypeptide and/or Fc portion of the compounds. Such derivatives may improve the solubility, absorption, biological half life, and the like of the compounds. The moieties may alternatively eliminate or attenuate any undesirable side-effect of the compounds and the like.

Exemplary derivatives include compounds in which:

1. The compound or some portion thereof is cyclic. For example, the pharmacologically active portion (i.e., peptide or polypeptide) may be modified to contain two or more Cys residues (e.g., in the linker), which could cyclize by disulfide bond formation. For citations to references on preparation of cyclized derivatives, see Table 2.

2. The compound is cross-linked or is rendered capable of cross-linking between molecules. For example, the pharmacologically active portion may be modified to contain one Cys residue and thereby be able to form an intermolecular disulfide bond with a like molecule. The compound may also be cross-linked through its C-terminus, as in the molecule shown below.

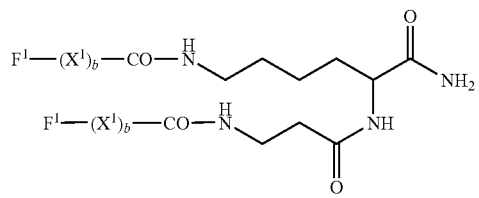

3. One or more peptidyl [—C(O)NR—] linkages (bonds) is replaced by a non-peptidyl linkage. Exemplary non-peptidyl linkages are —CH$_2$-carbamate [—CH$_2$—OC(O)N—], phosphonate, —CH$_2$-sulfonamide [—CH$_2$—S(O)$_2$NR—], urea [—NHC(O)NH—], —CH$_2$-secondary amine, and alkylated peptide [—C(O)NR$^6$— wherein R$^6$ is lower alkyl].

4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl—NH—(CBZ—NH—), wherein R and R$^1$ are each independently hydrogen or lower alkyl and wherein the phenyl ring may be substituted with 1 to 3 substituents selected from the group consisting of $C_1$-$C_4$ alkyl, $C_1$-$C_4$ alkoxy, chloro, and bromo.

5. The free C-terminus is derivatized. Typically, the C-terminus is esterified or amidated. Exemplary C-terminal derivative groups include, for example, —C(O)R$^2$ wherein R$^2$ is lower alkoxy or —NR$^3$R$^4$ wherein R$^3$ and R$^4$ are independently hydrogen or $C_1$-$C_8$ alkyl (preferably $C_1$-$C_4$ alkyl).

6. A disulfide bond is replaced with another, preferably more stable, cross-linking moiety (e.g., an alkylene). See, e.g., Bhatnagar et al. (1996), *J. Med. Chem.* 39:3814-9; Alberts et al. (1993) *Thirteenth Am. Pep. Symp.*, 357-9.

7. One or more individual amino acid residues is modified. Various derivatizing agents are known to react specifically with selected sidechains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), *J. Med. Chem.* 39:3814-9.

Derivatization with bifunctional agents is useful for cross-linking the peptides or their functional derivatives to a water-insoluble support matrix or to other macromolecular vehicles. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, *Proteins: Structure and Molecule Properties* (W. H. Freeman & Co., San Francisco), pp. 79-86 (1983).

Compounds prepared in the process of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Methods of Making

The compounds prepared in the process of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

This invention also contemplates that a vector capable of expressing the molecules in an appropriate host. The vector comprises the DNA molecule that codes for the molecule operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), *Chem. Polypeptides*, pp. 335-61 (Katsoyannis and Panayotis eds.); Merrifield (1963), *J. Am. Chem. Soc.* 85:2149; Davis et al. (1985), *Biochem. Intl.*

10:394-414; Stewart and Young (1969), *Solid Phase Peptide Synthesis*; U.S. Pat. No. 3,941,763; Finn et al. (1976), *The Proteins* (3rd ed.)2:105-253; and Erickson et al. (1976), *The Proteins* (3rd ed.) 2:257-527. Solid phase synthesis is the preferred technique of making individual peptides since it is the most cost-effective method of making small peptides.

Compounds that contain derivatized peptides or which contain non-peptide groups may be synthesized by well-known organic chemistry techniques.

Uses of the Compounds

In general. The compounds of this invention have pharmacologic activity resulting from the pharmacologically active molecules to which the Fc is attached. The activity of these compounds can be measured by assays known in the art.

In addition to therapeutic uses, the compounds of the present invention may also be useful in diagnosing diseases characterized by dysfunction of an associated protein of interest. In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a diagnostic kit to detect the presence of their associated proteins of interest in a biological sample. Such kits employ the compounds of the invention having an attached label to allow for detection. The compounds are useful for identifying normal or abnormal proteins of interest. For the EPO-mimetic compounds, for example, presence of abnormal protein of interest in a biological sample may be indicative of such disorders as Diamond Blackfan anemia, where it is believed that the EPO receptor is dysfunctional.

Pharmaceutical Compositions

In General. The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Pulmonary delivery forms. Also contemplated herein is pulmonary delivery of the Fc fusion molecules (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7:565-9; Adjei et al. (1990), *Internatl. J. Pharmaceutics* 63:135-44 (leuprolide acetate); Braquet et al. (1989), *J. Cardiovasc. Pharmacol.* 13 (suppl.5):s.143-146 (endothelin-1); Hubbard et al. (1989), *Annals Int. Med.* 3:206-12 ($\alpha$1-antitrypsin); Smith et al. (1989), *J. Clin. Invest.* 84:1145-6 ($\alpha$1-proteinase); Oswein et al. (March 1990), "Aerosolization of Proteins", *Proc. Symp. Resp. Drug Delivery II*, Keystone, Colo. (recombinant human growth hormone); Debs et al. (1988), *J. Immunol.* 140:3482-8 (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by. Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 $\mu$m (or microns), most preferably 0.5 to 5 $\mu$m, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the Fc fusion molecule is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages. The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

SPECIFIC PREFERRED EMBODIMENTS

Working Examples

The following disclosure(s) are illustrative rather than limiting.

Example 1

Identification of cysteines in a Fc construct of osteoprotegerin by CDAP labeling and alkaline-induced cleavage with LC-MS analysis Abstract Purpose. To assay for cysteines in a Fc construct of Osteoprotegerin stored in acidic media and to ascertain their location.

Methods. The reagent 1-cyano-4-dimethylamino-pyridinium tetrafluoroborate (CDAP) was employed to selectively cyanylate stable free-sulfhydryl groups at pH 4. Cyanylation reactions were analyzed by HPLC coupled with mass-spectral analysis (LC-MS). Reversed-phase HPLC was used to separate component peaks from the native and CDAP-reacted samples. The reversed-phase samples were collected, introduced into a solution of aqueous ammonium hydroxide plus guanidine hydrochloride and subsequently analyzed by LC-MS. Results. Reversed-phase HPLC analysis of Fc-Osteoprotegerin gave two peaks. LC-MS of the primary CDAP reaction revealed selective cyanylation of two-sulfhydryl groups in a peak that represents approximately 10% of the proteinaceous material; the peak representing approximately 90% of the material was not cyanylated after reaction with CDAP. Analysis of the ammonium/guanidine treated isoforms by LC-MS detailed the location of two free cysteine-sulfhydryl groups.

Conclusions. A reversed-phase separable form of Fc-Osteoprotegerin contains two free sulfhydryl groups. CDAP is an effective reagent for characterizing the free-sulfhydryl groups of proteins in acidic conditions.

Introduction

Fc-OPG, a construct of the naturally occurring cytokine Osteoprotegerin (OPG), is under clinical investigation for utility in the treatment of osteoporosis. Fc-OPG is a homodimeric, high molecular weight protein (91 kD) containing 24 cysteines in each monomer sequence. All cysteines in the dimer are covalently associated through 24 disulfide bonds (or cystine). These covalent linkages play a crucial role in maintaining the tertiary and quaternary structure of the protein. Therefore, unpaired cysteines may result in a decrease in biological activity, have immunogenic effects, or be a precursor to further physical and chemical instability (oxidation and aggregation).

Monitoring the state of cysteine side-chains—in the disulfide form of cystine or sulfhydryl of cysteine—is commonly accomplished by labeling the free sulfhydryl groups with a thiol specific fluorophor or molecular weight tag under alkaline conditions. Given the labile nature of cysteine-sulfhydryl groups and cystine-disulfides in alkaline aqueous media (pKa's~8), quantitative detection of free cysteine-sulfhydryl is subject to inaccuracy resulting from cystine reduction at high pH and cysteine related disulfide formation. Alkaline condition labeling methods may not be suitable for estimating the free-cysteine-sulfhydryl present in acidic formulations of proteins.

A reverse-phase HPLC separable isoform of Fc-OPG was observed to be reactive to the addition of aqueous $CuCl_2$. After reaction with $CuCl_2$, the isoform eluted with the same retention time as the main peak in the reverse-phase chromatogram. The nature of this reactivity led to speculation that the isoform was representative of free-sulfhydryl groups in the protein that were converted to cystine with the aid of a copper oxidant. Numerous techniques were employed to compare the number of free cysteine-sulfhydryl groups present in the main peak versus the isoform. No differences were found. A commonality between all of the techniques was the use of neutral to alkaline reaction conditions.

Figure 6:
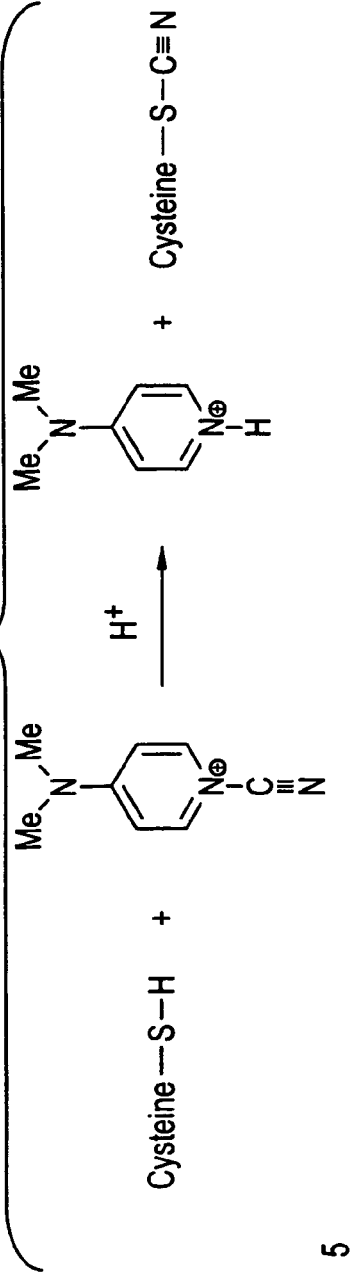
FIG. 6. Reaction scheme showing cyanylation of cysteine residues in acidic conditions with CDAP.
Figure 7:
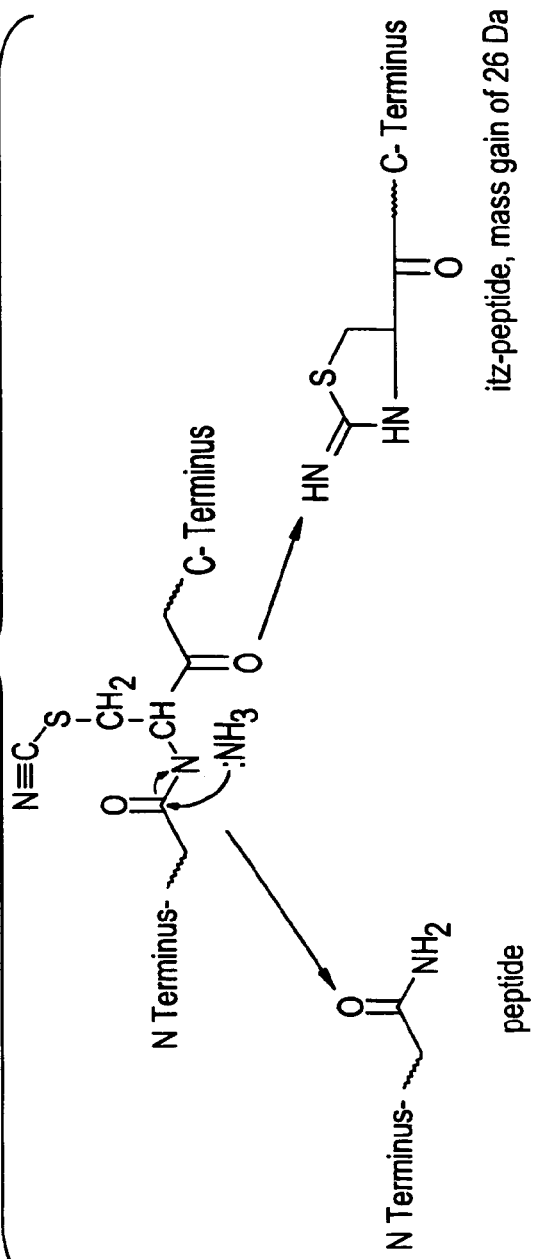
FIG. 7. Reaction scheme showing cleavage of the cyanylated cysteine by ammonia. Under alkaline and denaturing conditions (1.5N NH$_4$OH and 4M GdHCl), the protein backbone undergoes cleavage at the carbonyl-amide peptide bond on the cyanylated cysteine. The result is an amidated N-terminal peptide and an iminothiazolidine (ITZ) peptide which are separated and identified by LC-MS.

This example presents the characterization of the isoform using the reagent 1-cyano-4-dimethylamino-pyridinium tetrafluoroborate (CDAP). The detection and identification of unpaired cysteine residues present in acidic media is made possible by the cyanylation of free cysteine sulfhydryl groups by CDAP (FIG. 6) and subsequent peptide bond cleavage at the cyanylated cysteine residues (FIG. 7).

Materials

The Fc construct of OPG can be prepared by processes known in the art. CDAP can be purchased from Sigma-Aldrich (St. Louis, Mo).

Methods

RP-HPLC: Samples were injected into a Zorbax 300SB C8 4.6 mm×25 cm column and eluted with a gradient of 0.1% TFA and 0.1% TFA in 90% ACN at 60° C. on a Hewlett-Packard 1100 or 1090 at 215 nm.

Electrospray Mass Spectrometry: All mass spectrometry was performed on a Perkin-Elmer/Sciex AP100 spectrometer using conditions consistent with ionization of peptides and proteins.

Copper Treatment: Ten mg/ml protein in 10 mM sodium acetate and 5% sorbitol was treated with 50 mM $CuCl_2$ (final pH ~4).

Cyanylation Conditions: A solution of 50 mg/mL of CDAP in 0.5 M HCl was prepared. 50 µL of the CDAP solution was added to 500 µL of 10 mg/mL of protein in pH 5 acetate (10 mM) and 5% sorbitol. 5 µL of 0.1 N NaOH was added to the protein-CDAP mixture and vortexed.

Cleavage Conditions: The cyanylated protein was separated from native material by reverse-phase HPLC and both peaks were collected. The fractions were reduced in volume by approximately two-thirds under vacuum then treated with a solution of 1.5 M $NH_4OH$, 4 M GdHCl and heated at 37° C. for 90 minutes.

Discussion

Figure 8A:
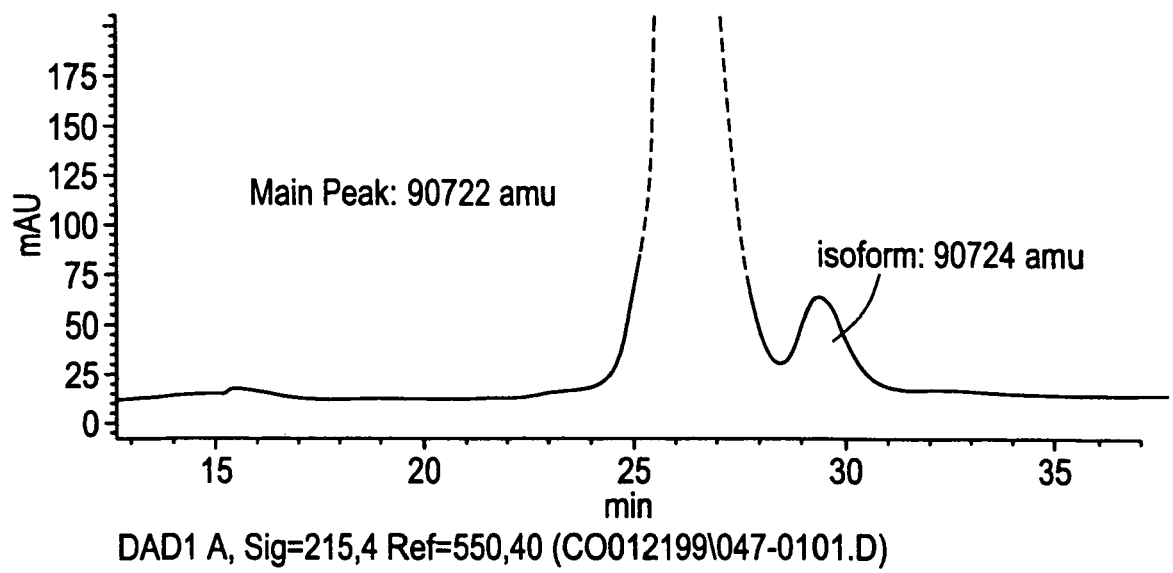
FIG. 8. RP-HPLC chromatograms with mass spectrometry determined molecular weights of Fc-OPG (A), Fc-OPG reacted with CuCl$_2$ (B), and Fc-OPG reacted with CDAP followed by CuCl$_2$ (C).
Figure 8B:
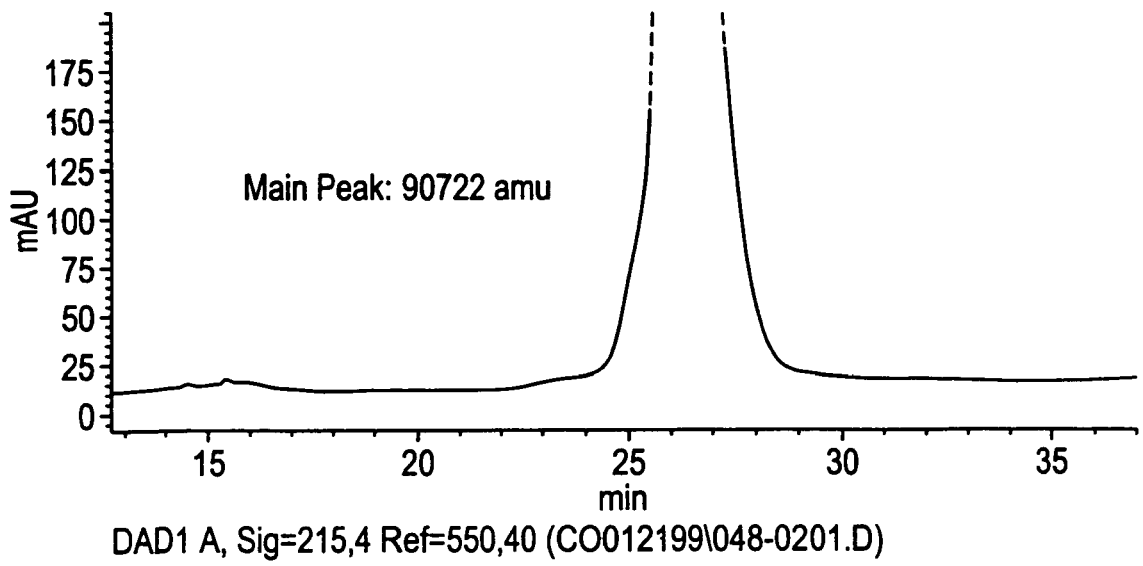
Figure 8C:
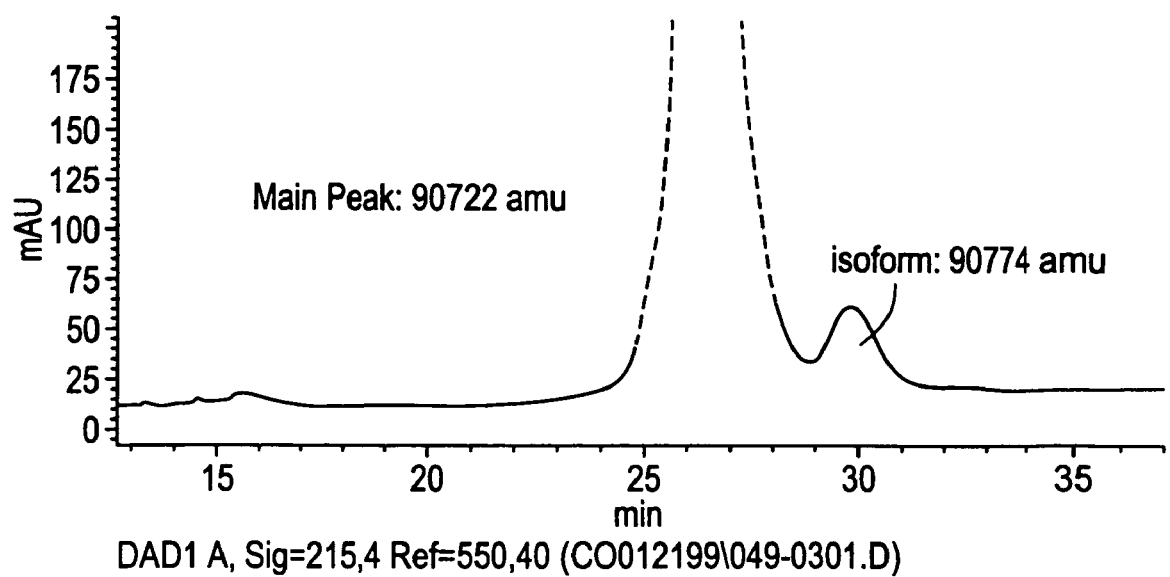

Cyanylation of two cysteine sulfhydryl groups in Fc-OPG would give a mass increase of 50 daltons resulting from the addition of two 26 dalton cyanide groups and the assumed loss of two protons from the cysteine side chains. The selective cyanylation of the RP-HPLC isoform is evident in the ~50 dalton mass increase detected for that peak; the main peak mass was unmodified. The nature of the isoform was further indicated by the observation that the isoform was no-longer responsive to the addition of $CuCl_2$. A pair of cyanylated cysteines would not be competent for disulfide formation via $CuCl_2$ oxidation (FIG. 8).

Figure 9:
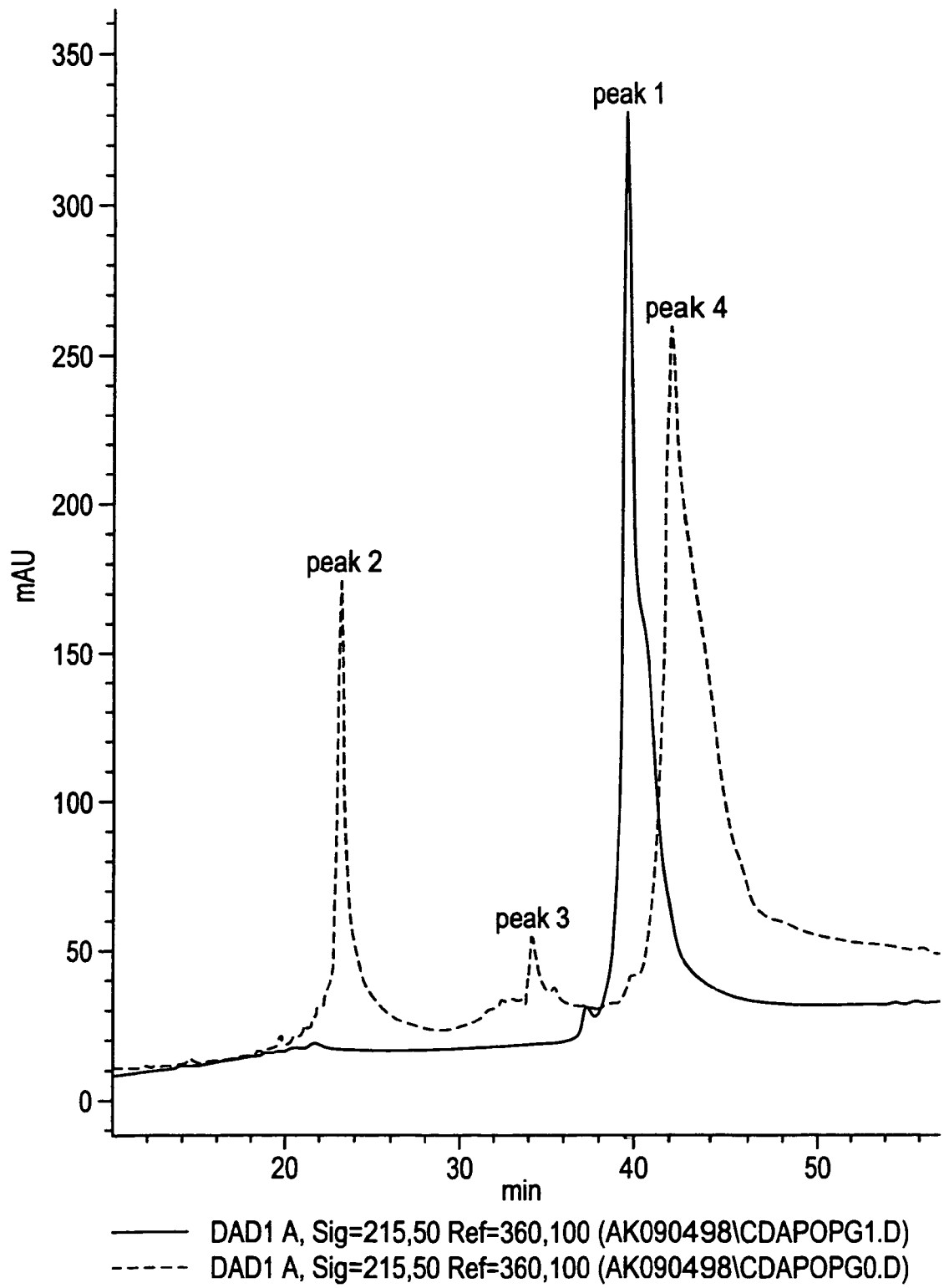
FIG. 9. RP-HPLC chromatograms of purified main and isoform peaks following CDAP reaction and cleavage.
Figure 10A:
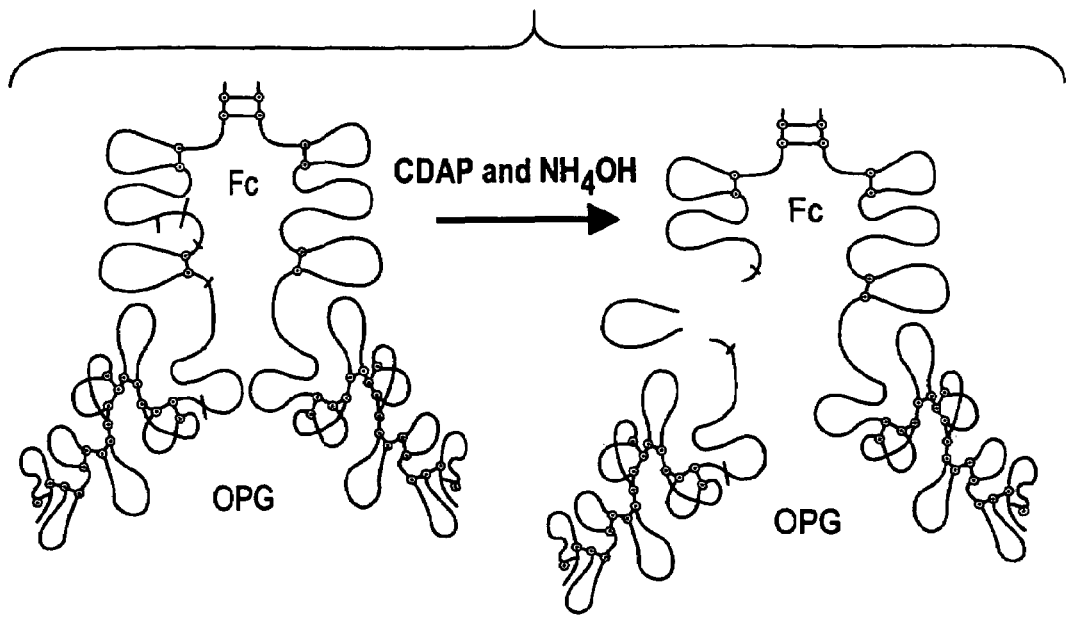
FIG. 10. Schematic diagram of the Fc-OPG construct, CDAP-cleavage pattern and the missing Fc-domain disulfide linkage that results in the RP-HPLC isoform.
Figure 10B:
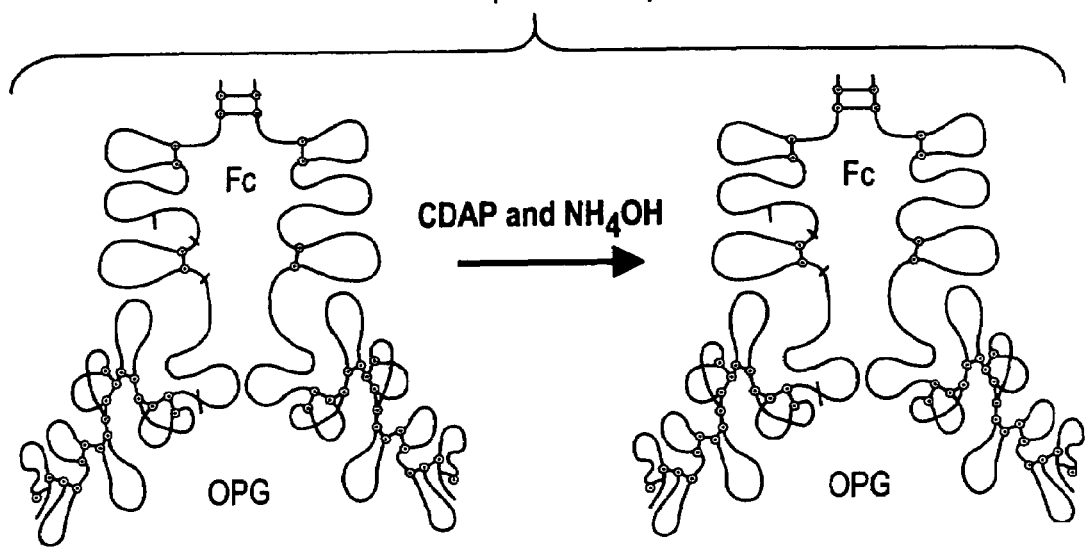

The cleavage pattern observed for the CDAP reacted and ammonium hydroxide treated isoform differed greatly from that of the main peak. The isoform cleavage reaction produced three distinct peaks and the main peak reaction resulted in one peak (FIG. 9). Mass spectrometry of the isoform cleavage products established their identity (Table 1). The peak with mass of 22,270 amu correlated with a fragment of the molecule consisting of the entire amino acid sequence C-terminal of the last cysteine in the Fc sequence (FIG. 9, peak 2). The mass found for peak 3 in FIG. 4, 6616.8 amu, is equivalent to the mass of a Fc-domain disulfide loop corresponding to the Fc sequence found N-terminally to the fragment determined for peak 2. Peak 4 (FIG. 9) correlates with the remaining piece of the Fc-OPG construct. These results reveal two free-cysteine-sulfhydryl groups in the Fc domain of one of the two monomers (FIG. 10).

In subsequent experiments, the RP-HPLC isoform was converted to main peak under alkaline-denaturing conditions (data not shown). Apparently, formation of cystine in the isoform was rapid enough in those alkaline conditions to go undetected by other techniques (Ellman's reaction and peptide mapping). The site specificity and acid-condition-compatibility of CDAP for labeling cysteine residues made possible the characterization of this protein isoform.

Conclusions

A reversed-phase HPLC separable isoform of Fc-OPG contains two free sulfhydryl groups. The detection of free cysteine sulfhydryl groups in a protein can be complicated by their transient nature in the alkaline conditions typically used for analysis. CDAP is an effective reagent for characterizing the free-sulfhydryl groups of proteins in acidic conditions.

Example 2

Purpose. Significant differences were observed in the stability of Fc-OPG as a function of copper treatment of the bulk protein, where Fc-OPG treated with copper was significantly more stable than Fc-OPG that was not. Specifically, the Fc-OPG that was not treated with copper was more prone to aggregation than the copper-treated Fc-OPG. The improved stability of Fc-OPG is thought to be due to the conversion of an unstable fraction of Fc-OPG with incomplete disulfide structure to a form with intact disulfide bonding upon treatment with copper ion.

Methods. Reversed-phase chromatography: Reversed-phase chromatography was performed on a Hewlett-Packard 1100 or 1090 HPLC system equipped with a diode-array detector and controlled by Chemstation Software. Fc-OPG samples were analyzed on a Zorbax (4.6 mm×25 cm) 300 SB column. The column is initially equilibrated at 90% buffer A (HPLC grade water containing 0.1% TFA). The samples were eluted with a linear gradient of 4.2% buffer B/min (90% acetonitrile, 10% HPLC grade water and 0.1% TFA) for 6 minutes then 0.11% buffer B/min over 37 minutes. The column was heated at 60° C. and elution was monitored 215 nm at a flow rate of 0.5 ml/min. Both copper and non-copper treated Fc-OPG (10 mg/mL) were formulated in 10 mM sodium acetate, pH 5.0, containing 5% sorbitol. Samples were incubated at 29° C. and analyzed over time.

Figure 11:
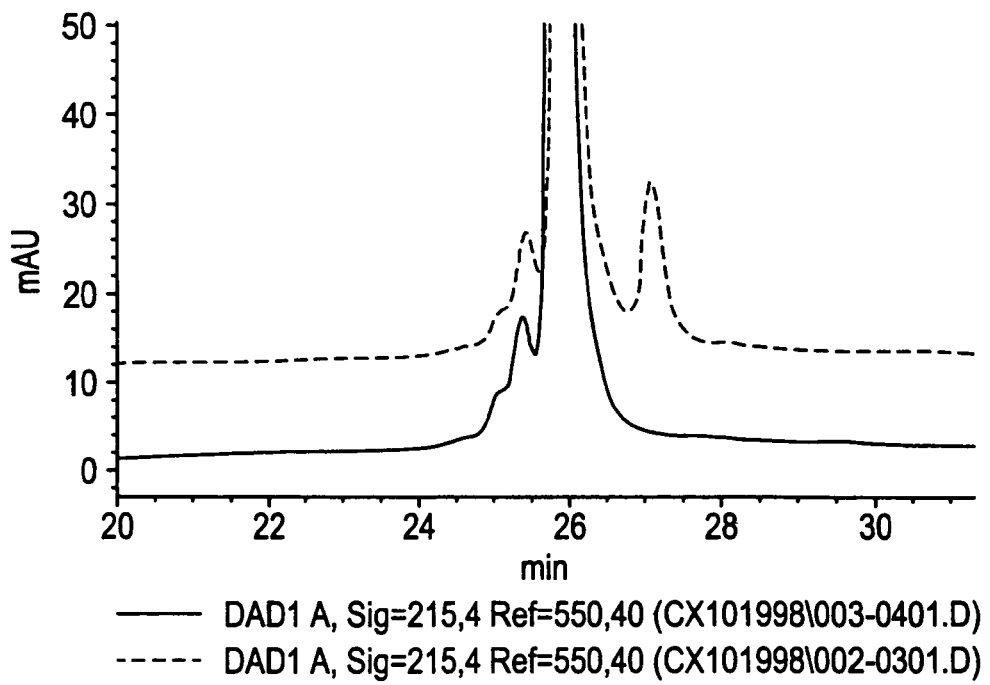
FIG. 11. Reversed-phase HPLC of untreated (upper trace) and copper-treated (lower trace) Fc-OPG.
Figure 12:
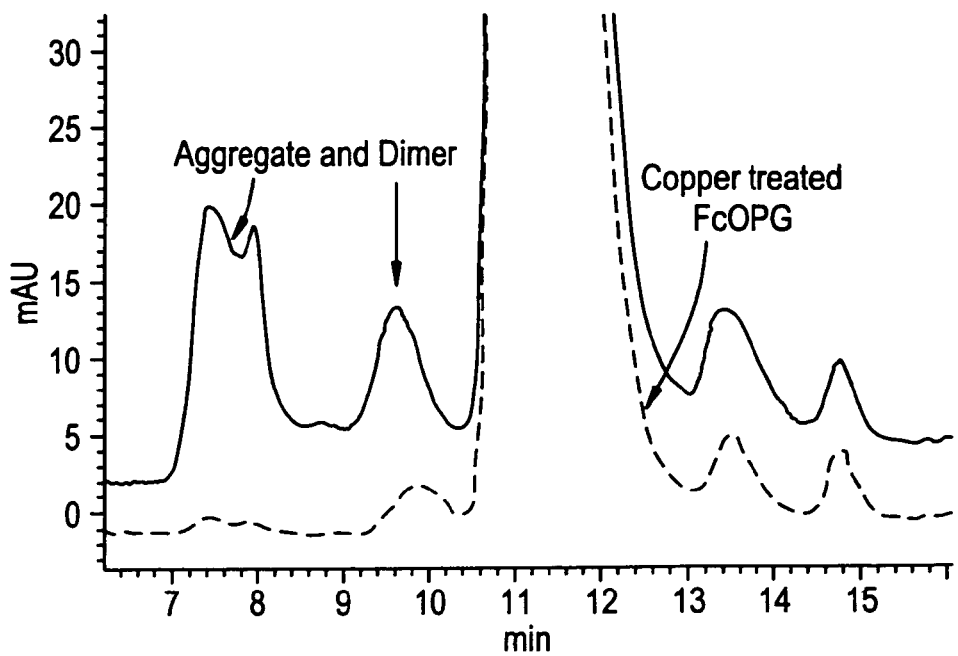
FIG. 12. Size-exclusion HPLC of Fc-OPG after 2 years incubation at 29° C.; copper-treated Fc-OPG (lower trace) and untreated Fc-OPG (upper trace).

Conclusions. As has been previously shown, $CuCl_2$ catalyzes the formation of cystine from two unpaired cysteines in Fc-OPG. The reversed-phase profiles of a Fc-OPG preparation after copper treatment versus one which was untreated are compared in FIG. 11. The prominent post-peak in the chromatogram of the untreated sample is due to the population of Fc-OPG molecules with unpaired cysteines. The stability of these Fc-OPG preparations was examined as a function of copper treatment by size-exclusion HPLC. The chromatograms of untreated and copper-treated Fc-OPG incubated at 29° C. for 2 years are shown in FIG. 12; an increase in high molecular weight aggregate and dimer peaks are evident in the untreated sample.

ABBREVIATIONS

The abbreviations used throughout this specification are defined as follows, unless otherwise defined in specific instances:

CDAP 1-cyano-4-dimethylamino-pyridinium tetrafluoroborate
HPLC high performance liquid chromatography
ITZ iminothiazolidine
OPG osteoprotegerin
RP reversed-phase
TNF tumor necrosis factor
TPO thrombopoeitin The invention now being fully described, it will be apparent to one of ordinary skill in the art that many changes and modifications can be made thereto, without departing from the spirit and scope of the invention as set forth herein.

What is claimed is:

1. A process for preparing a pharmacologically active compound, which comprises:
   (a) preparing an active compound which is a fusion molecule comprising a pharmacologically active domain and an Fc domain;
   (b) incubating the active compound with copper (II) chloride ($CuCl_2$) at a concentration from about 10 mM to 50 mM; and
   (c) subsequently isolating the active compound.

2. The process of claim 1, wherein the pharmacologically active compound is prepared in *Escherichia coli*.

3. The process of claim 2, wherein the $CuCl_2$ is used in a concentration of about 10 mM.

4. The process of claim 1, wherein the pharmacologically active compound is prepared in CHO cells.

5. The process of claim 4, wherein the $CuCl_2$ is used in a concentration of about 30 mM.

6. The process of claim 1, wherein the pharmacologically active domain comprises the sequence of an OPG protein.

7. The process of claim 1, wherein the pharmacologically active domain comprises the sequence of a leptin protein.

8. The process of claim 1, wherein the pharmacologically active domain comprises the sequence of a soluble TNF receptor.

9. The process of claim 1, wherein the pharmacologically active domain comprises the sequence of a soluble IL-1 receptor.

10. The process of claim 1, wherein the pharmacologically active domain comprises the sequence of an IL-1ra protein.

11. The process of claim 1, wherein the Fc domain is an IgG1 Fc domain.

12. The process of claim 1, wherein the Fc domain comprises the sequence of SEQ ID NO:2.

* * * * *